US009675415B2

(12) United States Patent
Varghese et al.

(10) Patent No.: US 9,675,415 B2
(45) Date of Patent: Jun. 13, 2017

(54) DEVICE FOR ENERGY-BASED SKIN TREATMENT

(71) Applicant: KONINKLIJKE PHILIPS N.V., Eindhoven (NL)

(72) Inventors: Babu Varghese, Eindhoven (NL); Rieko Verhagen, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 154 days.

(21) Appl. No.: 14/381,342

(22) PCT Filed: Feb. 19, 2013

(86) PCT No.: PCT/IB2013/051337
§ 371 (c)(1),
(2) Date: Aug. 27, 2014

(87) PCT Pub. No.: WO2013/128330
PCT Pub. Date: Sep. 6, 2013

(65) Prior Publication Data
US 2015/0038953 A1 Feb. 5, 2015

Related U.S. Application Data

(60) Provisional application No. 61/604,015, filed on Feb. 28, 2012.

(51) Int. Cl.
*A61B 18/20* (2006.01)
*A61B 5/00* (2006.01)
(Continued)

(52) U.S. Cl.
CPC .......... *A61B 18/203* (2013.01); *A61B 5/0059* (2013.01); *A61B 5/0077* (2013.01);
(Continued)

(58) Field of Classification Search
CPC ........................... A61B 18/203; A61B 5/0059
(Continued)

(56) References Cited

U.S. PATENT DOCUMENTS 4,984,229 A * 1/1991 Nedvidek ............ G11B 7/0917
369/121
5,847,394 A * 12/1998 Alfano .................. A61B 1/042
250/341.1
(Continued)

FOREIGN PATENT DOCUMENTS

| JP | 2009236610 A | 10/2009 |
|---|---|---|
| WO | 2006101736 A1 | 9/2006 |
| WO | 2008001284 A2 | 1/2008 |

OTHER PUBLICATIONS

Wikipedia, Laser-induced breakdown spectroscopy, Apr. 19, 2010.*
(Continued)

*Primary Examiner* — Christopher A Flory
*Assistant Examiner* — Jonathan Kuo

(57) ABSTRACT

A device (10) for energy-based skin treatment is provided. The device (10) comprises a light source (18) for providing polarized incident light (21) having an incident polarization, optical elements (11, 12, 13) for focusing the polarized incident light (21) in a focal point (22) within a collagen layer of the skin (30), a polarization-sensitive detection unit (41, 42) for selectively detecting a selected polarization component of light of a generated harmonic (23) of the polarized incident light (21) returning from the skin (30), and a processor, at least being coupled to the polarization-sensitive detection unit (41, 42), for determining a depth of the focal point (22) within the collagen layer based on the detected selected polarization component.

13 Claims, 2 Drawing Sheets

(51) Int. Cl.
*G01N 21/21* (2006.01)
*G01N 21/47* (2006.01)
*A61B 18/00* (2006.01)
*A61N 5/01* (2006.01)
*A61N 5/073* (2006.01)

(52) U.S. Cl.
CPC ......... *G01N 21/21* (2013.01); *G01N 21/4795* (2013.01); *A61B 2018/0047* (2013.01); *A61B 2018/00738* (2013.01); *A61N 2005/073* (2013.01)

(58) Field of Classification Search
USPC ..................................... 606/9–11; 607/88–95
See application file for complete search history.

(56) References Cited

U.S. PATENT DOCUMENTS

| | | | |
|---|---|---|---|
| 6,287,774 B1 * | 9/2001 | Nikiforov | C12Q 1/37 204/155 |
| 7,460,248 B2 | 12/2008 | Kurtz | |
| 2005/0163365 A1 * | 7/2005 | Barbour | G01B 11/24 382/154 |
| 2006/0241495 A1 | 10/2006 | Kurtz | |
| 2010/0016688 A1 | 1/2010 | Debreczeny | |
| 2010/0113941 A1 * | 5/2010 | Hendriks | A61B 5/0075 600/478 |

OTHER PUBLICATIONS

Yasui, Sasaki, Tohno, Araki, "Tomographic Imaging of Collagen Fiber Orientation in Human Tissue Using Depth-Resolved Polarimetry of Second-Harmonic-Generation Light", Dec. 2005, Optical and Quantum Electronics, 37: 1397. doi:10.1007/s11082-005-4219-0.*

Psilodimitrakopoulos Sotiris et al: "Three-dimensional polarization second harmonic generation (3D-SHG) imaging: the effect of the tilted-off the plane SHG active structures", Multiphoton Microscopy in the Biomedical Sciences XI, SPIE, 1000 20th St. Bellingham WA 98225-6705 USA, vol. 7903, No. 1, Feb. 10, 2011 (Feb. 10, 2011), pp. 1-8, XPO60007642, DOI: 10.1117/12.875254 [retrieved on Feb. 10, 2011] abstract.

* cited by examiner

DEVICE FOR ENERGY-BASED SKIN TREATMENT

This application is the U.S. National Phase application under 35 U.S.C. §371 of International Application No. PCT/IB2013/051337, filed on Feb. 19, 2013, which claims the benefit of U.S. Provisional Application No. 61/604,015 filed on Feb. 28, 2012. These applications are hereby incorporated by reference herein.

FIELD OF THE INVENTION

This invention relates to a device for energy-based skin treatment, the device comprising a light source for providing incident light and optical elements for focusing the incident light in a focal point within a collagen layer of the skin.

This invention further relates to a method and a computer program product for determining a treatment depth within a collagen layer of a skin.

BACKGROUND OF THE INVENTION

Such a skin treatment device is, e.g., known from the published international patent application WO 2008/001284 A2. Said application discloses a skin treatment device with a laser source and focusing optics. The device creates a focal spot in a dermis layer of the skin to be treated. The power of the laser source and the dimensions of the focal spot are selected such that laser induced optical breakdown (LIOB) affects the skin in order to stimulate re-growth of skin tissue and reduce wrinkles. It is also disclosed to provide image sensors for detecting wrinkles before the laser light is applied to the skin.

The focal point is created at a fixed treatment depth, somewhere between 0.2 and 2.0 mm. This depth is selected based on the typical composition of human skin. In some cases, however, the optimal treatment depth may be different. The optimal treatment depth depends on, e.g., the thickness of the stratum corneum and the epidermis. If superficial lesions are created above the dermis, micro-rupturing of capillaries may cause petechiae or other adverse side effects may occur. This will lead to an increased social down time. Furthermore, treatment at a non-optimal depth is detrimental to the efficacy of the treatment.

If the light induced damages are selectively created in the collagen fibers of the dermis, the efficacy of the treatment can be increased with a minimum of side effects.

OBJECT OF THE INVENTION

It is an object of the invention to provide a device for energy-based skin treatment which provides an improved treatment result and/or reduced side effects.

SUMMARY OF THE INVENTION

According to a first aspect of the invention, this object is achieved by providing a device for energy-based skin treatment. The device comprises a light source for providing polarized incident light having an incident polarization, optical elements for focusing the polarized incident light in a focal point within a collagen layer of the skin, a polarization-sensitive detection unit for selectively detecting a selected polarization component of light of a generated harmonic of the polarized incident light returning from the skin, and a processor, at least being coupled to the polarization-sensitive detection unit, for determining a depth of the focal point within the collagen layer based on the detected selected polarization component.

The use of the polarization-sensitive detection unit for measuring selected polarization components of the generated harmonic enables detection of the collagen in the dermis. In the skin, only the collagen generates the harmonics of the incident light. Second harmonic generation (SHG) causes light with half the wavelength (double the frequency) of the incident light to return from the skin. Also third harmonics (three times the frequency) and higher harmonics are produced. When focused at shorter focusing depths inside the collagen, the polarization of the generated harmonics will be the same as the incident polarization. At larger focusing depths inside the collagen, the generated harmonic will be depolarized due to scattering. Consequently, for larger focusing depths the ratio of parallel polarized light (parallel to the incident polarization) to randomly or otherwise differently polarized light will decrease. According to the invention, this effect is used to determine the depth of the focal point in the collagen layer.

By selectively detecting certain polarization components and, based thereon, determining how far the light is depolarized due to scattering by the collagen, the collagen content and focus depth inside the collagen are determined. Predetermined relations between the depth of focus and loss of polarization may be used for determining the depth of the focus within the collagen layer. Determining the amount of depolarization can be done in different ways, depending on the exact polarization or polarizations for which the detector is sensitive. Some exemplary methods will be described below. All such methods have in common that for at least one, preferably two, specific polarization directions the amount of light having that polarization direction is measured. Such methods may also include using a further detector measuring light regardless of its polarization.

In one embodiment of the device according to the invention, the polarization-sensitive detection unit comprises two channels, a first one of the two channels being arranged to selectively detect a polarization component corresponding to the incident polarization and a second one of the two channels being arranged to detect a polarization component orthogonal to the incident polarization. When the incident light is focused at the epidermis, no SHG (or other harmonics) light is detected at all. When the incident light is focused at the upper part of the dermis, the signal in the detector for the incident polarization will be high and the signal in the detector for the orthogonal polarization will be relatively low. As the focus moves deeper into the layer, the SHG light is depolarized and the ratio of the signals from both detectors approaches 1. A polarizing beam splitter may be used to separate the two orthogonal states of polarization and thereby provide the desired depth contrast.

In a different embodiment the polarization-sensitive detection unit comprises a polarization rotator for changing a polarization of the light of the generated harmonic and the polarization-sensitive detection unit is arranged to selectively detect the selected polarization component for at least two different settings of the polarization rotator. This embodiment also uses the depolarization of the SHG light at larger focusing depths. When the SHG light is depolarized, the polarization rotator will not affect the signal detected by the polarization-sensitive detector. At smaller focusing depths in the dermis, the SHG light is highly polarized and will only be detected by the polarization-sensitive detector when the polarization is rotated to an angle that corresponds to a polarization for which the detector is sensitive. When the polarization is rotated to an angle orthogonal to the angle for which the detector is sensitive, the signal from the detection unit will be minimal.

Alternatively, a polarization rotator is provided for changing the incident polarization and the polarization-sensitive detection unit is arranged to selectively detect the selected polarization component of the generated harmonic for at least two different settings of the polarization rotator. This embodiment works in a similar way as the previous one. At focusing depths at which the incident light is depolarized, the SHG light will be detected regardless of the polarization direction. At smaller focusing depths, the light will only be detected if the (rotated) incident polarization corresponds to the polarization for which the detector is sensitive. If rotating the polarization of the incident light, preferably over 90 degrees, leads to a different signal from the polarization-sensitive detection unit, the incident light is focused at a higher part of the dermis than when rotating the polarization does not have any effect on the detection signal.

Although the best, i.e. most accurate, results may be obtained by determining a ratio of the amount of detected light at two different polarizations, e.g. incident and orthogonal, also the difference between the two amounts could provide a good indication of the optimum treatment depth. Alternatively, detected light of one polarization direction is compared to a total amount of detected light. Again, both differences and ratios may be used. It is to be noted that the detection of a generated second harmonic is already disclosed in the published Japanese patent application JP 2009/236610 A. However, in this Japanese application, the generated second harmonic is only used for non-invasively evaluating a state of wrinkles on a skin. Statistical distributions of orientations of collagen fibers at different depths are used for evaluating the state of the wrinkles Although, the polarization of the incident light is varied for gathering information about the orientations, the Japanese application does not disclose polarization-sensitive detection units or determining optimum depths for light based skin treatment.

Based on the detected depth of the focal point inside a collagen layer of the skin, and a predetermined optimal treatment depth for the energy-based skin treatment, a controllable focusing device may adjust the depth of the focal point. For this purpose, in an embodiment of the device for energy-based skin treatment comprising a main energy source for treatment of the skin and a controllable focusing device for focusing treatment energy generated by the main energy source into the collagen layer of the skin, the processor is further arranged to determine a difference between the determined depth of the focal point and a predetermined optimal treatment depth within the collagen layer and to control the controllable focusing device based on said difference. As already described above it may be important for the efficacy of the treatment and for minimizing adverse side effects, that the skin treatment takes place at the optimal depth inside the skin. If the energy-based skin treatment, e.g., uses laser induced optical breakdown (LIOB), the treatment depth may be adapted by, e.g., mechanically manipulating optical elements for directing and focusing the laser beam. Also for other types of energy sources, such as RF or ultra-sound, it is possible and desirable to adapt the focusing depth.

Optionally, the incident light is further provided for providing optical energy to the collagen layer for skin treatment. In an embodiment, the optical energy may induce optical breakdown of skin cells which causes light flashes with an emission spectrum. In such an embodiment, the device may further comprise light source tuning apparatus for tuning a wavelength, an intensity, or a pulse duration of the incident light, such that overlap of the emission spectrum with a wavelength spectrum of the light of the generated harmonic is reduced. In one embodiment, the light source tuning apparatus can comprise separate light sources used for treatment and detection, respectively.

The optical breakdown of skin tissue by short flashes of incident light causes a hot plasma to be generated. The black body radiation emitted by this hot plasma depends on the plasma temperature which depends on the wavelength, pulse duration and pulse intensity of the incident light. If the emitted spectrum of the black body radiation overlaps the spectrum of the SHG light, the SHG light is more difficult to detect. It is therefore desirable to tune the incident light such that the SHG light can easily be detected.

An optical filter may be provided for selectively passing the light of the generated harmonic. The optical filter may comprise a harmonic separator or an optical band-pass filter. By passing the SHG light (and/or possibly further harmonics) and not other light with wavelengths too far away from that of the SHG light, the accuracy of the detection is improved. The optical filter may, for example, be used to separate the SHG light from the black body radiation caused by the optical breakdown of skin tissue.

According to a further aspect of the invention, a method and a computer program product for determining a treatment depth within a collagen layer of a skin are provided. The method comprises providing polarized incident light with an incident polarization, focusing the polarized incident light in a focal point within a collagen layer of the skin, selectively detecting a selected polarization component of light of a generated harmonic of the incident light returning from the skin, and determining the depth of the focal point within the collagen layer of the skin based on the detected polarization component.

These and other aspects of the invention are apparent from and will be elucidated with reference to the embodiments described hereinafter.

DETAILED DESCRIPTION OF THE INVENTION

Figure 1:
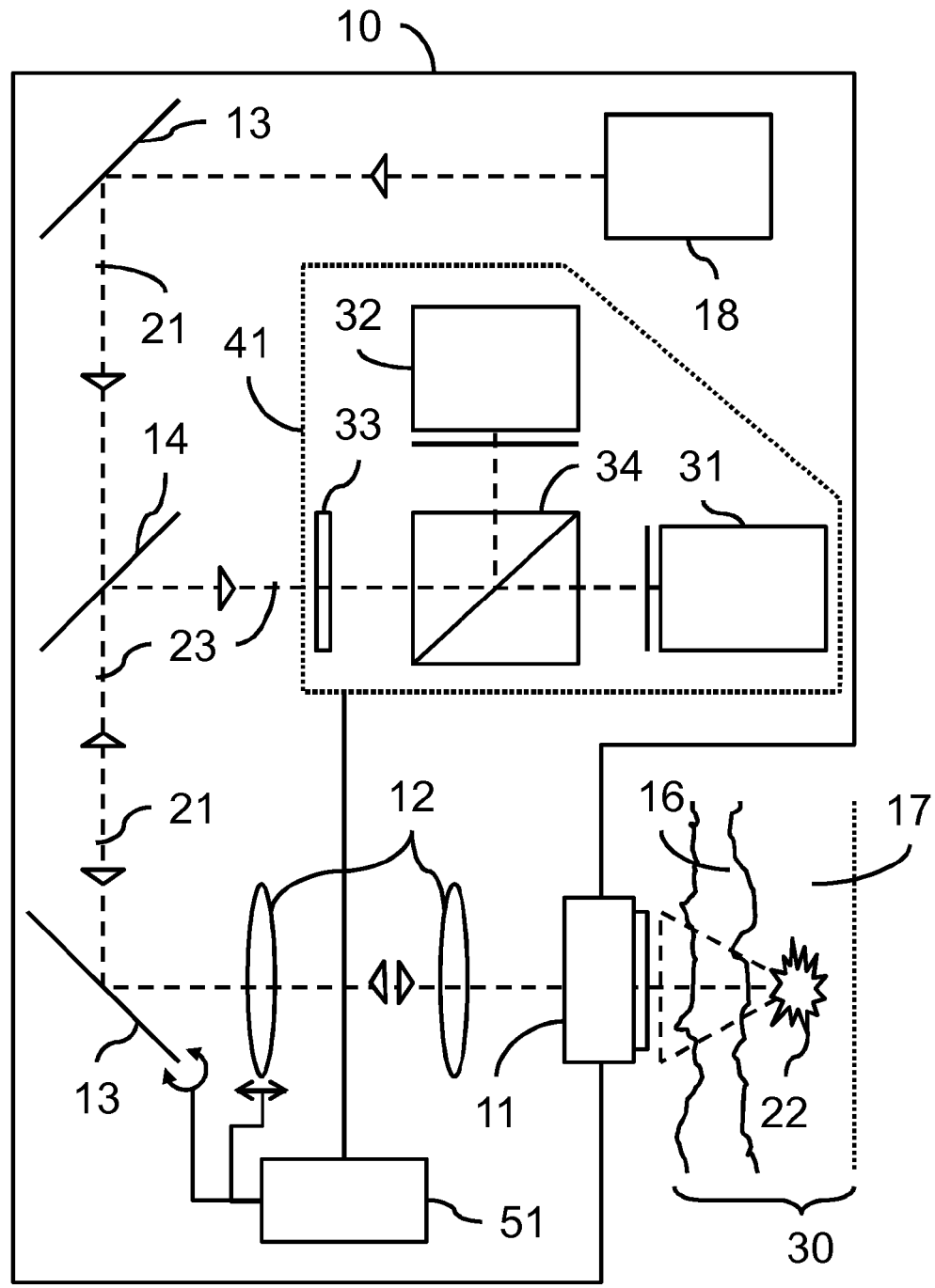
FIG. 1 schematically shows a skin treatment device according to the invention.

FIG. 1 schematically shows a skin treatment device 10 according to the invention. The device 10 comprises a light source 18 for providing incident light 21 for treating human or animal skin 30. The incident light beam 21 is typically a pulsed laser beam with an incident polarization. The incident light 21 may, e.g., have a circular or linear polarization. For example, Nd:YAG lasers with emission at 1064 nm are used for light induced optical breakdown (LIOB) skin treatment. Optical elements 11, 12, 13 are provided for focusing the pulsed laser beam 21 inside the skin 30. In the embodiment described here, the light source 18 is both suitable for providing the skin treatment and for determining a depth of the focal point within the collagen layer. However, it is to be noted that the focal depth detection may use a separate light source which may operate at a different power level and/or at different wavelengths. For example, picosecond diode lasers are readily available that might be very suitable for the focal depth detection. It is to be noted that instead of treating the skin by the use of light, the device may also use other energy sources such as RF or ultra-sound.

The skin 30 comprises multiple layers with different optical properties. The epidermis 16 is composed of the outermost layers and forms a waterproof protective barrier. Underneath the epidermis 16, the dermis 17 is situated. The dermis 17 comprises the collagen fibers at which the skin treatment is aimed. The purpose of the skin treatment is to create a focus 22 of the pulsed laser beam 21 in the collagen of the dermis 17 in order to create microscopic lesions which result in new collagen formation.

Part or all of the optical elements 11, 12, 13 may be provided in an interface element 11 which, during use of the device 10, is pressed onto or makes contact with the skin 30 to be treated. The optical elements may comprise lenses 12 for converging and/or diverging the incident light beam 21 and mirrors 13 for deflecting the light beam 21 into a desired direction. The exact position and/or orientation of the optical elements may be controllable in order to make it possible to adapt the position and the quality of the focus 22 as required for obtaining the desired LIOB creation inside the dermis 17. Focus control means 51 may be provided for, e.g., moving one or more of the lenses 12 and/or rotating one or more of the mirrors 13 in order to control the position of the focal point 22 inside the skin 30.

In addition to the above described more or less usual elements of optical skin treatment devices 10, the optical skin treatment device 10 according to the invention further comprises a polarization-sensitive detection unit 41 for detecting SHG (second harmonic generation) light 23. SHG light 23 is created in nonlinear optical processes in which photons interacting with a nonlinear material are effectively combined to form new photons with twice the energy, and therefore twice the frequency and half the wavelength of the initial photons. This phenomenon also occurs in the collagen fibers in the dermis 17. In addition to second harmonics, also third and higher harmonics are generated. In the following, all references to SHG light shall be understood to also encompass third and higher harmonics.

The polarization-sensitive detection unit 41 of the skin treatment device according to the invention is provided for detecting the SHG light coming back from the skin. A harmonic separator 14 may be provided for separating the SHG light from, e.g., light directly reflected at the skin 30 surface. Alternatively or additionally, a filter 33 may be used for only passing the SHG light. With a 1064 nm incident light beam 21 and a corresponding 532 nm SHG response, a cut off filter 33 with a stop wavelength around 600 nm may be used to ensure that only SHG light will be registered by the detection unit 41. Another source of light that could interfere with the SHG detection is the black body radiation emitted by hot plasma created by the LIOB of skin tissue. The laser pulses 21 used for the skin treatment typically lead to short visible flashes in the range 300-1500 nm. This light can be filtered out by using a narrow band pass filter 33. However, the overlap between the spectra of these short visible flashes and of the SHG light can be avoided by tuning i.e. via a light source tuning apparatus, separate light sources, etc.), e.g., the wavelength, intensity or pulse duration of the incident light. The peak of the black body radiation spectrum can be shifted to lower or higher wavelengths by tuning the temperature of the hot plasma caused by the LIOB. The plasma temperature depends on tunable properties of the incident light 21. Furthermore, low intensity pulses that do not create LIOB may be used just for creating SHG light for detecting collagen before starting the skin treatment or during short pauses of the treatment.

For determining a depth position of the focal point 22 in the collagen layer (i.e., collagen fibers) of the dermis 17, the polarization of the detected SHG light is an important parameter. The incident light beam 21 has a well defined incident polarization. At small focusing depths inside the collagen (i.e., collagen fibers of the dermis layer of the skin 30, the SHG light maintains this incident polarization. At larger depths, approximately above 100 μm, the SHG light becomes depolarized. Consequently, at smaller depths, the polarization-sensitive detection unit 41 only detects a SHG signal when looking at one specific polarization component. At larger depths, the SHG signal is independent of the polarization. With the polarization-sensitive SHG detection according to the invention, this depolarizing property of the collagen is used to detect a depth position of the focal point inside the collagen layer (i.e., collagen fibers) of the dermis 17.

The polarization-sensitive detection unit 41 in FIG. 1 comprises, in addition to the cut off or band pass filter 33, a polarizing beam splitter 34 for splitting the SHG light 23 into two beams with different polarization. A first beam, e.g. with the incident polarization, is detected by a first photo detector 31. A second beam with a different, preferably orthogonal, polarization is detected by a second photo detector 32. The first and second photo detectors 31, 32 may comprise polarization filters for ensuring that each channel only registers the SHG light with the correct polarization. At small depths, only the first detector 31 will detect the SHG light 23. At larger depths, the signal from the second detector 32 will increase while the signal from the first detector 31 decreases. When the focus 22 is at a depth where the SHG light 23 is completely depolarized, the ratio, R, of the signals from both detectors 31, 32 will be 1.

Before or during use of the skin treatment device, an exact focal depth may be determined based on, e.g., a predetermined relation between depth of the focal point and the detected polarization component(s) or their ratio, R. The processor (not shown) and/or the focus control means 51 may compare the determined focal depth with a predetermined optimal treatment depth. If the processor makes this comparison and calculates the required change of focal depth, the focus control means 51 may receive instructions for adapting the focus position from the processor. Alternatively, the processor only provides the detected focal depth as input to the focus control means 51 and the focus control means 51 calculate the required adaptations to the optical elements 12, 13. In a further example, the detected polarization components are directly provided to the focus control means 51 by the polarization-sensitive detection unit 41, 42 and the focus control means 51 calculate both the current focal depth and the required measures for correcting it.

The optimal treatment depth within the collagen layer of the dermis 17 or other treatment parameters, such as intensity or duration, may depend on the user and the exact purpose of the treatment. For example, the user's age and skin condition may be important. With the accurate detection of the depth of the focal point 22 within the dermis 17 by the device according to the invention, the optimal treatment parameters can be determined and adjusted with improved accuracy. Focal depth detection may continue during treatment or may be repeated during short intervals between two periods of treatment.

Figure 2:
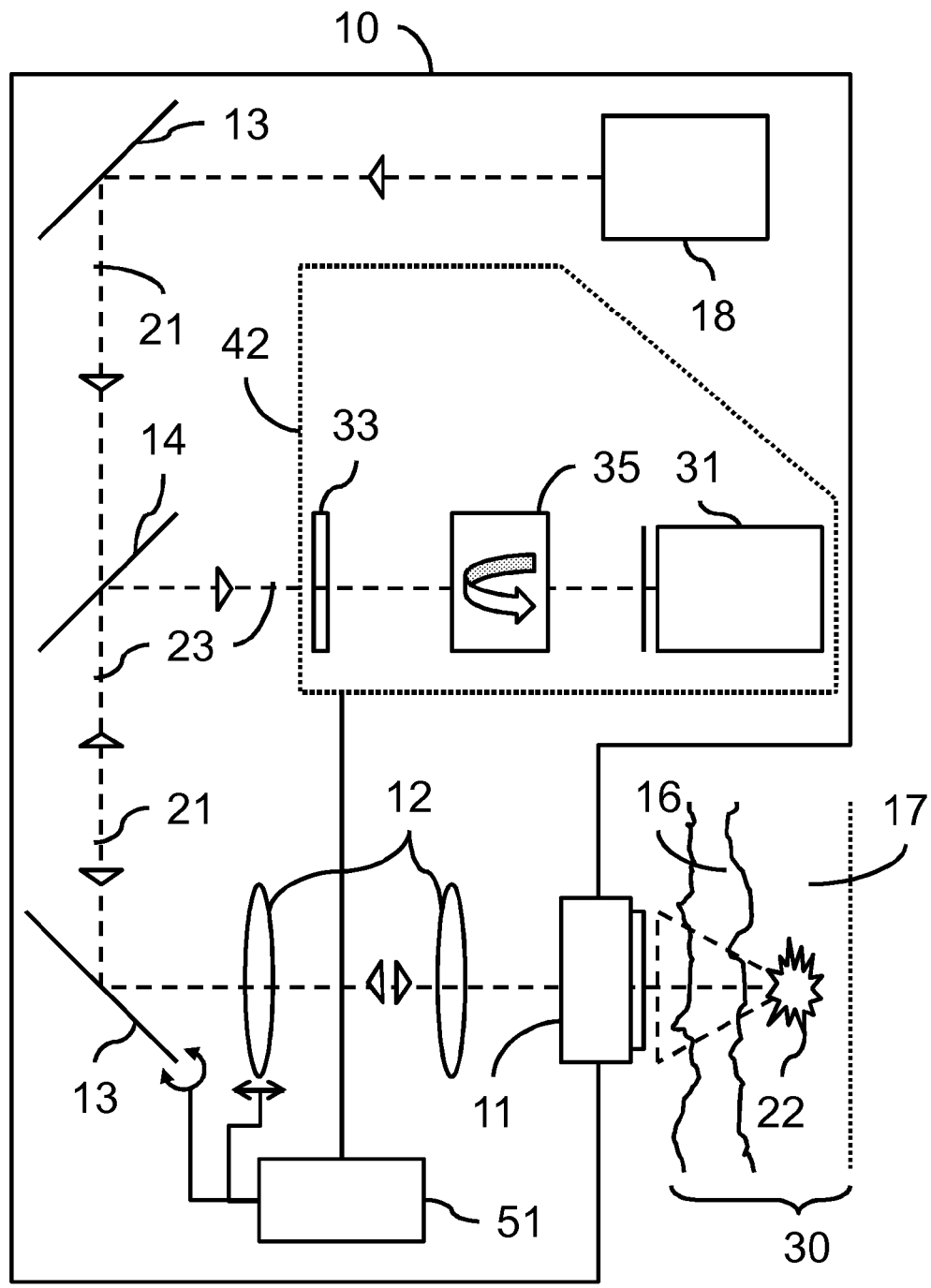
FIG. 2 shows a similar skin treatment device with an alternative polarization-sensitive detection unit.

FIG. 2 shows a similar skin treatment device 10 with an alternative polarization-sensitive detection unit 42. This detection unit only uses one polarization dependent photo detector 31. This one photo detector 31 is used in combination with a controllable polarization rotator 35. At smaller focusing depths, the signal from the photo detector 31 will depend on the configuration of the polarization rotator 35. In a particular configuration of the polarization rotator 35, the signal from the polarization dependent photo detector 31 will be at a maximum. At orthogonal configurations, the signal will be significantly decreased and may even approach 0. At larger depths, when the SHG light 23 becomes depolarized, the signal from the photo detector 31 will be independent of the configuration of the polarization rotator 35. The same results can be obtained by using the polarization rotator 35 for rotating the polarization of the incident light beam 21 instead of the polarization of the SHG light 23.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. It will also be appreciated that such a program may have many different architectural designs. For example, a program code implementing the functionality of the method or system according to the invention may be subdivided into one or more subroutines. Many different ways to distribute the functionality among these subroutines will be apparent to the skilled person. The subroutines may be stored together in one executable file to form a self-contained program. Such an executable file may comprise computer executable instructions, for example processor instructions and/or interpreter instructions (e.g. Java interpreter instructions). Alternatively, one or more or all of the subroutines may be stored in at least one external library file and linked with a main program either statically or dynamically, e.g. at run-time. The main program contains at least one call to at least one of the subroutines. Also, the subroutines may comprise function calls to each other. An embodiment relating to a computer program product comprises computer executable instructions corresponding to each of the processing steps of at least one of the methods set forth. These instructions may be subdivided into subroutines and/or be stored in one or more files that may be linked statically or dynamically. Another embodiment relating to a computer program product comprises computer executable instructions corresponding to each of the means of at least one of the systems and/or products set forth. These instructions may be subdivided into subroutines and/or be stored in one or more files that may be linked statically or dynamically.

The carrier of a computer program may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A device for energy-based skin treatment, the device comprising:
    a light source for providing polarized incident light having an incident polarization;
    optical elements for focusing the polarized incident light in a focal point within a collagen layer of the skin such that only the collagen layer generates second or higher harmonics of the polarized incident light;
    a polarization-sensitive detection unit for selectively detecting a selected polarization component of light of a generated second or higher harmonic of the polarized incident light returning from the skin, wherein the selected polarization component of light comprises both (i) a polarization component corresponding to the incident polarization and (ii) a polarization component orthogonal to the incident polarization; and
    a processor, at least being coupled to the polarization-sensitive detection unit, for determining a depth of the focal point within the collagen layer based on the detected selected polarization component that comprises both (i) the polarization component corresponding to the incident polarization and (ii) the polarization component orthogonal to the incident polarization, wherein determining the depth includes determining (a) a ratio of an amount of detected light at the incident polarization and an amount of detected light at the orthogonal to the incident polarization, or (b) a difference between the two amounts.

2. The device for energy-based skin treatment as claimed in claim 1, wherein the processor is further arranged to determine the depth of the focal point within the collagen layer from a predetermined relation between the depth and at least the selected polarization component.

3. The device for energy-based skin treatment as claimed in claim 1, further comprising a main energy source for treatment of the skin and a controllable focusing device for focusing treatment energy generated by the main energy source into the collagen layer of the skin, wherein the processor is further arranged to determine a difference between the determined depth of the focal point and a predetermined optimal treatment depth within the collagen layer and to control the controllable focusing device based on said difference.

4. The device for energy-based skin treatment as claimed in claim 1, wherein the polarization-sensitive detection unit further comprises two channels, a first one of the two channels being arranged to selectively detect a polarization component corresponding to the incident polarization and a second one of the two channels being arranged to detect a polarization component orthogonal to the incident polarization.

5. The device for energy-based skin treatment as claimed in claim 1, wherein the polarization-sensitive detection unit further comprises a polarization rotator for changing a polarization of the light of the generated second or higher harmonic, and wherein the polarization-sensitive detection unit is further arranged to selectively detect the selected polarization component for at least two different settings of the polarization rotator.

6. The device for energy-based skin treatment as claimed in claim 1, further comprising:
a polarization rotator for changing the incident polarization, wherein the polarization-sensitive detection unit is further arranged to selectively detect the selected polarization component of the generated second or higher harmonic for at least two different settings of the polarization rotator.

7. The device for energy-based skin treatment as claimed in claim 4, wherein the polarization-sensitive detection unit is further arranged to determine the depth of the focal point based on a ratio between the polarization components detected by the two channels.

8. The device for energy-based skin treatment as claimed in claim 5, wherein the polarization-sensitive detection unit is further arranged to determine the depth of the focal point based on a ratio between the selected polarization components detected for the at least two different settings of the polarization rotator.

9. The device for energy-based skin treatment as claimed in claim 1, wherein the polarization-sensitive detection unit further comprises an optical filter for selectively passing the light of the generated second or higher harmonic of the polarized incident light returning from the skin.

10. The device for energy-based skin treatment as claimed in claim 9, wherein the optical filter further comprises a harmonic separator or an optical band-pass filter.

11. The device for energy-based skin treatment as claimed in claim 1, wherein the light source is further arranged for providing optical energy to the collagen layer for skin treatment.

12. The device for energy-based skin treatment as claimed in claim 11, wherein the optical energy is provided to induce an optical breakdown effect in the collagen layer causing light flashes with an emission spectrum, and wherein the device further comprises a light source tuning apparatus that includes separate light sources used for treatment and detection, respectively, wherein the light source tuning apparatus is configured via use of the separate light sources, to tune a wavelength, a light intensity or a pulse duration of the incident light, such that an overlap of (i) the emission spectrum and (ii) a wavelength spectrum of the generated second or higher harmonic of the polarized incident light is reduced.

13. A method for determining a treatment depth within a collagen layer of a skin, the method comprising
providing, via a light source, polarized incident light with an incident polarization,
focusing, via optical elements; the polarized incident light in a focal point within a collagen layer of the skin such that only the collagen layer generates second or higher harmonics of the polarized incident light;
selectively detecting, via a polarization-sensitive detection unit, a selected polarization component of light of a generated second or higher harmonic of the incident light returning from the skin, wherein the selected polarization component of light comprises both (i) a polarization component corresponding to the incident polarization and (ii) a polarization component orthogonal to the incident polarization; and
determining, via a processor coupled to the polarization-sensitive detection unit, the depth of the focal point within the collagen layer of the skin based on the detected selected polarization component that comprises both (i) the polarization component corresponding to the incident polarization and (ii) the polarization component orthogonal to the incident polarization, wherein determining the depth includes determining (a) a ratio of an amount of detected light at the incident polarization and an amount of detected light at the orthogonal to the incident polarization, or (b) a difference between the two amounts.

* * * * *